(12) United States Patent
Benk et al.

(10) Patent No.: US 10,603,426 B2
(45) Date of Patent: Mar. 31, 2020

(54) DEVICE WITH A BAG-SHAPED CONTAINER AND METHOD FOR FILLING A PUMP-OPERATED HOLLOW LINE-SUPPORTED LIQUID CIRCUIT WITHOUT FORMING GAS BUBBLES USING THE DEVICE

(71) Applicant: ResuSciTec GmbH, Freiburg (DE)

(72) Inventors: Christoph Benk, Freiburg (DE); Jürgen Grudke, Krefeld (DE); Joel Louoba, Auggen (DE)

(73) Assignee: RESUSCITEC GMBH, Freiburg (DE)

( * ) Notice: Subject to any disclaimer, the term of this patent is extended or adjusted under 35 U.S.C. 154(b) by 370 days.

(21) Appl. No.: 15/516,354

(22) PCT Filed: Oct. 1, 2015

(86) PCT No.: PCT/EP2015/072720
§ 371 (c)(1),
(2) Date: Mar. 31, 2017

(87) PCT Pub. No.: WO2016/050924
PCT Pub. Date: Apr. 7, 2016

(65) Prior Publication Data
US 2017/0296735 A1  Oct. 19, 2017

(30) Foreign Application Priority Data
Oct. 2, 2014 (DE) .......................... 10 2014 014 725

(51) Int. Cl.
*A61M 1/36* (2006.01)
*A61M 1/16* (2006.01)

(52) U.S. Cl.
CPC ........ *A61M 1/3627* (2013.01); *A61M 1/1698* (2013.01); *A61M 1/3643* (2013.01); *A61M 1/3644* (2014.02); *A61M 1/3647* (2014.02)

(58) Field of Classification Search
CPC .............. A61M 1/1698; A61M 1/3627; A61M 1/3643; A61M 1/3644; A61M 1/3647
See application file for complete search history.

(56) References Cited

U.S. PATENT DOCUMENTS

| | | | | |
|---|---|---|---|---|
| 4,734,269 A | * | 3/1988 | Clarke ................ | A61M 1/3627 128/DIG. 3 |
| 4,863,452 A | * | 9/1989 | Irmiter ................ | A61M 1/3627 604/408 |
| 5,061,236 A | * | 10/1991 | Sutherland .......... | A61M 1/3627 210/436 |
| 5,573,526 A | * | 11/1996 | Hess .................... | A61M 1/3624 128/DIG. 3 |
| 5,695,489 A | * | 12/1997 | Japuntich ............ | A61M 1/3627 604/403 |

(Continued)

*Primary Examiner* — Benjamin J Klein
(74) *Attorney, Agent, or Firm* — Fitch, Even, Tabin & Flannery LLP (57) ABSTRACT

The invention relates to a container in the form of a bag having a flexible bag wall at least in a region, in which a first and a second hollow channel section, pass through the bag wall in a fluid-tight manner, wherein the hollow channel sections respectively have an open channel end that is located within the container for connecting the open channel ends to one another in a separable and fluid-tight manner.

18 Claims, 2 Drawing Sheets

(56) References Cited

U.S. PATENT DOCUMENTS

| | | | |
|---|---|---|---|
| 5,858,015 A * | 1/1999 | Fini | A61J 1/10 |
| | | | 128/DIG. 24 |
| 7,429,325 B2 * | 9/2008 | Ingvarsson | A61M 1/3627 |
| | | | 210/136 |
| 2006/0054557 A1 * | 3/2006 | Hori | A61M 1/3636 |
| | | | 210/645 |

* cited by examiner

DEVICE WITH A BAG-SHAPED CONTAINER AND METHOD FOR FILLING A PUMP-OPERATED HOLLOW LINE-SUPPORTED LIQUID CIRCUIT WITHOUT FORMING GAS BUBBLES USING THE DEVICE

CROSS-REFERENCE TO RELATED APPLICATIONS

Reference is made to International Application No. PCT/EP2015/072720 filed Oct. 1, 2015, and German Patent Application No. 102014014725.8, filed Oct. 2, 2014, which applications are incorporated herein by reference in their entirety.

BACKGROUND OF THE INVENTION

Field of the Invention

The invention relates to a device with a bag-shaped container having bag wall which is flexible at least in a region, in which first and a second hollow channel sections pass through the bag wall in a fluid-tight manner. Both hollow channel sections respectively have an open channel end within the bag with the open channel ends being designed for being connected to one another in a separable and fluid-tight manner. The device particularly serves for filling a pump-operated, hollow line-supported liquid circuit with a liquid without forming gas bubbles. In this context, a method is followed for filling a pump-operated, hollow line-supported liquid circuit, into which preferably an oxygenator is integrated, with a liquid without forming gas bubbles with the device.

Description of the Prior Art

Publication DE 33 47 183 A1 discloses a method and a device for connecting filling tubes, particularly for blood or the like, without forming gas bubbles. A flexible, fluid-tight bag is used for this purpose, wherein two tube ends of a hollow line system protrude through its bag wall in a fluid-tight manner and end in the interior of the bag in an open manner. The hollow line system is filled by of the bag, wherein the bag and the tube ends protrude into the bag and assume the highest position relative to the gravitational force vector in the hollow line system during the filling process. In this way, gas bubbles that may be enclosed in the liquid and therefore entrained thereby, particularly in the form of air bubbles, can escape through the tube ends within the bag as a result of buoyancy. After a certain holding period for the buoyancy-driven degassing process, the two tube ends are connected within the bag volume filled with liquid in a fluid-tight manner. This ensures that both tube ends do not have any contact with air while the connection is produced. To this end, the flexible bag wall is light-transparent such that the connecting process can be carried out manually and visually monitored.

U.S. Pat. No. 4,734,269 discloses a bag-shaped device for degassing a liquid flow conveyed within a hollow line-supported liquid circuit. The bag has a self-contained volume, into which a supply line and a discharge line extend at a distance from one another. The line openings of the supply and discharge lines are respectively designed flush with the inner bag wall. A filter element is furthermore arranged within the bag in a fixed manner, wherein the filter wall of the filter element partially encloses a filter volume and is designed in the form of an open pocket in the region opposite of the supply line such that a liquid flowing into the bag through the supply line is directed into the filter volume. During the flow-related passage of the liquid through the filter wall into the remaining bag volume, the filter wall separates potential gas fractions that can escape through an upper hollow degassing line, which protrudes into the bag and into the filter volume. The liquid is degassed after it flows through the filter wall due to the filter effect and recirculated through the open discharge line leading into the bag volume.

U.S. Pat. No. 5,573,526 discloses a reservoir bag for a liquid, particularly for storing blood supplies to be connected to extracorporeal or cardiopulmonary circulatory systems in a fast and safe fluidic manner. Similar to the above-described bag system, this reservoir bag features a filter insert within the bag volume, wherein a supply line passes through the bag wall in a fluid-tight manner and leads into the filter volume of the filter insert, which is enclosed by a filter wall. The filter insert encloses a filter volume that is separated from the remaining bag volume, wherein a degassing line passes through the bag in a fluid-tight manner and leads into the upper volume region of the filter volume. The filter volume is separated from the remaining bag volume by of the filter wall such that liquid can reach the remaining bag volume free of bubbles due to the filter effect and then be fed in to an extracorporeal circulatory system through the discharge line leading into the remaining bag volume.

U.S. Pat. No. 5,935,093 discloses a cardiotomy container, the design of which is optimized so that the quantity of priming liquid, which is required for producing a fluidic connection to the oxygenator of a heart/lung machine without forming gas bubbles, can be minimized in order to thereby minimize negative effects on the patient connected to the heart/lung machine. This cardiotomy container has three volumes which are a mixing volume, a storage volume and a cardiotomy volume. The cardiotomy volume is provided with a filter/defoaming arrangement and filled with cardiotomy blood, which subsequently fills the storage volume, through a cardiotomy inlet port. Venous blood of the patient reaches the mixing volume through inlet ports arranged thereon and is mixed with the cardiotomy blood from the storage volume in the mixing volume. The mixed blood ultimately reaches the patient through an outlet port arranged on the mixing volume. The cardiotomy container serves as intermediate buffer volume for the operation of a heart/lung machine, in which potential blood flow differences in the extracorporeal circulatory system can be compensated.

SUMMARY OF THE INVENTION

The invention enhances a device according to above-cited publication DE 33 47 183 A1, in which a bag-shaped container has a flexible bag wall at least in a region, in which two hollow channel sections pass through the bag wall in a fluid-tight manner. Both hollow channel sections respectively have an open channel end within the bag and these open channel ends are respectively designed for being connected to one another in a separable and fluid-tight manner, such that a pump-operated, hollow line-supported liquid circuit can be quickly filled without forming gas bubbles.

When pump-operated hollow line-supported liquid circuits having in some instances a large volume that has to be filled as quickly as possible without forming gas bubbles, the liquid has to be pumped through the hollow line-supported liquid circuit with high transport speeds. In this case, flow speeds of five to ten liters per minute occur, but such high flow speeds lead to significant problems with the degassing process, as well as with subsequently producing a connection between two liquid-filled tube ends without forming gas bubbles, if conventional filling methods are used. The invention therefore provides an option that makes it possible to quickly fill a pump-operated, hollow line-supported liquid circuit, in which it is ensured that the connection between both open channel ends located within the bag can be produced without forming gas bubbles.

A device in accordance with the invention with a bag-shaped container, is hereafter referred to as bag has a first filter insert which is introduced within the bag and at least partially encompasses a first inner filter volume with a first filter wall within a volume that is at least partially encompassed by the bag, which is referred to as a bag volume. A tubular fluid line section passes through the first filter wall and is locally connected thereto The fluid line section is open on both sides and indirectly or directly leads into the first filter volume on one side and directly into the bag volume on the other side. In addition, the channel end of the first hollow channel section, which is located within the bag, is designed for connection to the open fluid line section leading into the bag volume in a separable and fluid-tight manner.

The inventive bag therefore can be distinguished from the device for connecting two filling tubes without forming air bubbles known from above-cited publication DE 33 47 183 A1 at least in that a first filter insert is provided within the bag volume with a tubular fluid line section, connected to the first filter wall, which allows a fluidic connection between the first inner filter volume and the remaining bag volume. In addition to producing the fluidic connection between these two volumes, however, the tubular fluid line section particularly also serves as a connection piece for connection to the first hollow channel section leading into the bag in a separable and fluid-tight manner such that the channel end of the first hollow channel section can, depending on the respective requirements, either be connected to the first filter volume or alternatively to the open channel end of the second hollow channel section leading into the bag in a fluid-tight manner via the tubular fluid line section. In this way, the device of the invention combines two different functions, namely the function of degassing a liquid flowing with interspersed gas bubbles that flows through the bag-shaped device of the invention with high flow speed on the one hand and the function of connecting two liquid-filled hollow channel sections in a fluid-tight manner without forming gas bubbles on the other hand.

The tubular fluid line section is advantageously connected to the first filter insert in a locally rigid, but otherwise self-supporting manner and the first filter wall peripherally encloses an outer wall assigned to the tubular fluid line section in a fluid-tight manner. Consequently, the connecting region between the fluid line section and the first filter wall does not contain any opening in the filter wall, through which an unfiltered exchange of liquids between the bag volume surrounding the first filter insert and the first filter volume can take place.

In order to connect the channel end of the first hollow channel section, which is located within the bag, to the open fluid line section leading into the bag volume in a fluid-tight manner, the first hollow channel section is preferably made of a material that is more rigid than the material, from which the tubular fluid line section is made. The tubular fluid line section is preferably made of a biocompatible PVC material while the first hollow channel section is made of polycarbonate. Due to the different elasticities of these materials, the more flexible tubular fluid line section can be pushed onto the channel end of the first hollow channel section located within the bag in a fluid-tight manner. Alternatively, it is naturally also possible to reverse the described material selection.

It is alternatively also conceivable to connect the open channel ends of the first hollow channel section and of the tubular fluid line section leading into the bag volume in a fluid-tight manner by use of a fluid connector. In this case, both sides of the connector have conically tapered connector ends that can be respectively fitted into the open channel ends such that a fluid-tight clamped and frictionally engaged connection is produced. Such a fluid connector may on one side also be rigidly and inseparably connected to one of the two channel ends.

The bag wall is designed to be flexible at least in the region, in which the first and second hollow channel sections pass through the bag wall, and furthermore is a light-transparent material such that the handling of the bag, particularly connecting and separating the channel ends of both hollow channel sections located in the bag and the tubular fluid line section, can be manually carried out from the outside through the bag wall and at the same time visually monitored.

In order to respectively connect or couple the two open channel ends of the first and the second hollow channel sections, which are located within the bag, these open channel ends also have different material elasticities such that the open channel ends of both hollow channel sections can be fitted into one another in a fluid-tight manner in order to connect these open channel ends without forming gas bubbles.

The first filter insert preferably is rigidly fixed within the bag volume and includes a filter screen or so-called screening filter having a filter wall preferably having a filter pore size between 20 and 200 µm, particularly 40, 80 or 120 µm. The filter wall may completely enclose the first inner filter volume, but it is likewise possible to design the first filter insert in a bag-like or sack-like manner. That is the filter wall features an opening on one side in this case, preferably having an upper opening that lies opposite of the lower filter bag bottom, on which the fluid line section protrudes through the filter wall.

In order to improve the filter effect, that is the attainable degassing of a liquid flowing into the filter volume by use of the filter insert, it has proved advantageous to introduce at least one second filter insert within the first filter volume, particularly for high flow speeds, wherein the second filter insert at least partially encloses a second filter volume with a second filter wall, into which the fluid line section leading into the first filter volume leads. Analogous to the first filter wall, the second filter wall also locally borders on the fluid line section in a fluid-tight manner.

According to the further comments on the filter effect, the second filter insert not only serves for realizing a two-stage degassing process, in which a liquid flowing into the second filter volume is subjected to a first filtering process as it passes through the second filter wall and to a second filtering process as it subsequently passes through the first filter wall and gas fractions are respectively retained or separated during each filtering process. The second filter insert can also reduce the flow pressure that otherwise would act unabatedly upon the first filter wall. The liquid flow within the first filter volume can thereby also be influenced. The two-stage filter effect may, if so required, also be optimized with additional filter inserts and is particularly effective for fluid flow speeds of 5 liters per minute or more.

In order to discharge the gas fractions separated within at least the first filter volume, at least one degassing line leads into the first filter volume and makes it possible to discharge the gas fractions. A second degassing line may optionally be provided and lead into the second filter volume through the first and the second filter insert in order to discharge gas fractions accumulating in the second filter volume.

If the bag has to be filled with a liquid that subsequently serves for filling a pump-operated, hollow line-supported liquid circuit, at least one filling line leading into the first filter volume is provided. While passing through the first filter wall, the supplied liquid flows from the first filter volume into the surrounding bag volume, from which the liquid is subsequently fed to an external liquid circuit through the second hollow channel section. Additional fluid lines, which preferably lead into the first filter volume, may also be provided depending on the respective application.

The aforementioned degassing, filling and fluid lines, which are hollow lines, advantageously lead into a region of the first filter volume that lies diametrically opposite of the fluid line section. In all practical applications, the bag is always oriented vertically relative to the gravitational force vector such that all aforementioned hollow lines lead into the first filter volume above the fluid line section. Other details regarding the physical design of the inventive bag-shaped device can be gathered from the description of the exemplary embodiments illustrated in the drawings.

In a preferred application, the inventive device serves for filling a pump-operated, hollow line-supported liquid circuit with a liquid without forming gas bubbles, wherein the hollow line-supported liquid circuit is interrupted at one point and has two fluid line ends, one of which represents a supply line and the other one of which represents a discharge line of the hollow line-supported liquid circuit. In order to connect the bag-shaped device of the invention to the pump-operated, hollow line-supported liquid circuit to be filled in a fluid-tight manner, the first and the second hollow channel section respectively have a channel end that is located outside the bag and designed for being respectively connected to the supply and discharge lines of the hollow line-supported liquid circuit. Material combinations that differ with respect to their elastic properties may also be considered for producing a fluid-tight connection between both hollow line sections and the supply and discharge lines of the liquid circuit such that the lines can be respectively inserted into one another in a fluid-tight manner. Any other known fluid-tight flange connections such as, e.g., Luer-Lock connections or the like may naturally also be provided.

The device of the invention particularly serves for filling a pump-operated, hollow line-supported liquid circuit, into which an oxygenator is integrated in order to oxygenate the blood of a patient.

The invention also proposes a method for filling a pump-operated, hollow line-supported liquid circuit with a liquid without forming gas bubbles by use of the above-described device, wherein the hollow line-supported liquid circuit is interrupted at one point and has two fluid line ends, one of which represents a supply line and the other one of which represents a discharge line of the hollow line-supported liquid circuit.

The inventive method is characterized by the succession of the following steps:

The above-described inventive bag, in which the open channel end of the first hollow channel section can be or is connected to the fluid line section in a fluid-tight manner within the bag, is initially supplied. Subsequently, the supply line is connected to the first hollow channel section and the discharge line is connected to the second hollow channel section of the bag in a fluid-tight manner. The hollow line-supported liquid circuit is then filled with a liquid by introducing the liquid into the first filter volume, wherein the liquid subsequently flows into the adjacent bag volume through the first filter wall and from there into the discharge line of the hollow line-supported liquid circuit, in which the liquid is transported in the direction from the discharge line to the supply line in a pump-operated manner. In this way, the liquid flows into the first or, if applicable, the second filter volume through the supply line, the first hollow channel section and the fluid line section.

The filling process is completed once the hollow line-supported liquid circuit has been completely filled and the bag has been at least partially filled. The pump-operated liquid circuit is also sustained after the filling process has been completed until the entire amount of liquid within the hollow line-supported liquid circuit and within the bag has passed through the at least first filter wall at least once, preferably multiple times.

Due to the light-transparent design of the bag wall, it can be visually monitored if separation of gas bubbles takes place within the filter. Once the separation of gas bubbles apparently comes to a halt, this is a first indication that the liquid conveyed within the hollow line-supported liquid circuit is completely free of gas bubbles. In this case, the first hollow channel section is manually separated from the fluid line section and the open ends of the first and second hollow channel sections located within the bag are subsequently connected to one another in a fluid-tight manner. This separation and reconnection take place within the liquid-filled region of the bag volume in order to ensure that no gas inclusions whatsoever occur while the first and the second hollow channel section are connected. Depending on the respective situation and external circumstances, the separation and reconnection may also be carried out during the operation of the liquid circuit by use of the pump or after a corresponding standstill of the liquid circuit. Due to the flexible bag wall, all manipulations required for the separation and connection can be carried out from the outside through the bag wall.

If a second filter insert is provided within the first filter insert as described above in order to enhance the filter effect, the liquid supplied to the bag through the supply line of the hollow line-supported liquid circuit is initially introduced into the second filter volume. The liquid only reaches the first filter volume after flowing through the second filter wall and/or through a corresponding opening within the second filter wall, wherein the liquid then flows through the first filter wall and into the remaining bag volume, from which the liquid is returned to the hollow line-supported liquid circuit, into which an oxygenator is preferably integrated, through the second hollow channel section and the discharge line connected thereto in a fluid-tight manner.

After the first and the second hollow channel section have been connected within the bag without forming gas bubbles, the bag can be emptied and, if so required, at least partially removed from the hollow channel sections. For this purpose, suitably separable predetermined breaking points or joining regions are respectively provided on the fluid-tight connecting regions between the first and second hollow channel sections and the bag wall.

In addition to quickly filling a pump-operated, hollow line-supported liquid circuit, into which an oxygenator for oxygenating patient blood is integrated, without forming gas bubbles in the above-described manner, the inventive bag-shaped device can also be used for filling any closed liquid circuits in the field of science and technology. This merely requires a corresponding adaptation of the channel ends of the first and second hollow channel sections, which are located outside the bag, to the respective external connecting structure of the supply and discharge lines.

BRIEF DESCRIPTION OF THE DRAWINGS

Exemplary embodiments of the invention are described below with reference to the drawings, but the general inventive concept is not limited to the described exemplary embodiments. In these drawings.

DETAILED DESCRIPTION OF THE INVENTION

Figure 1:
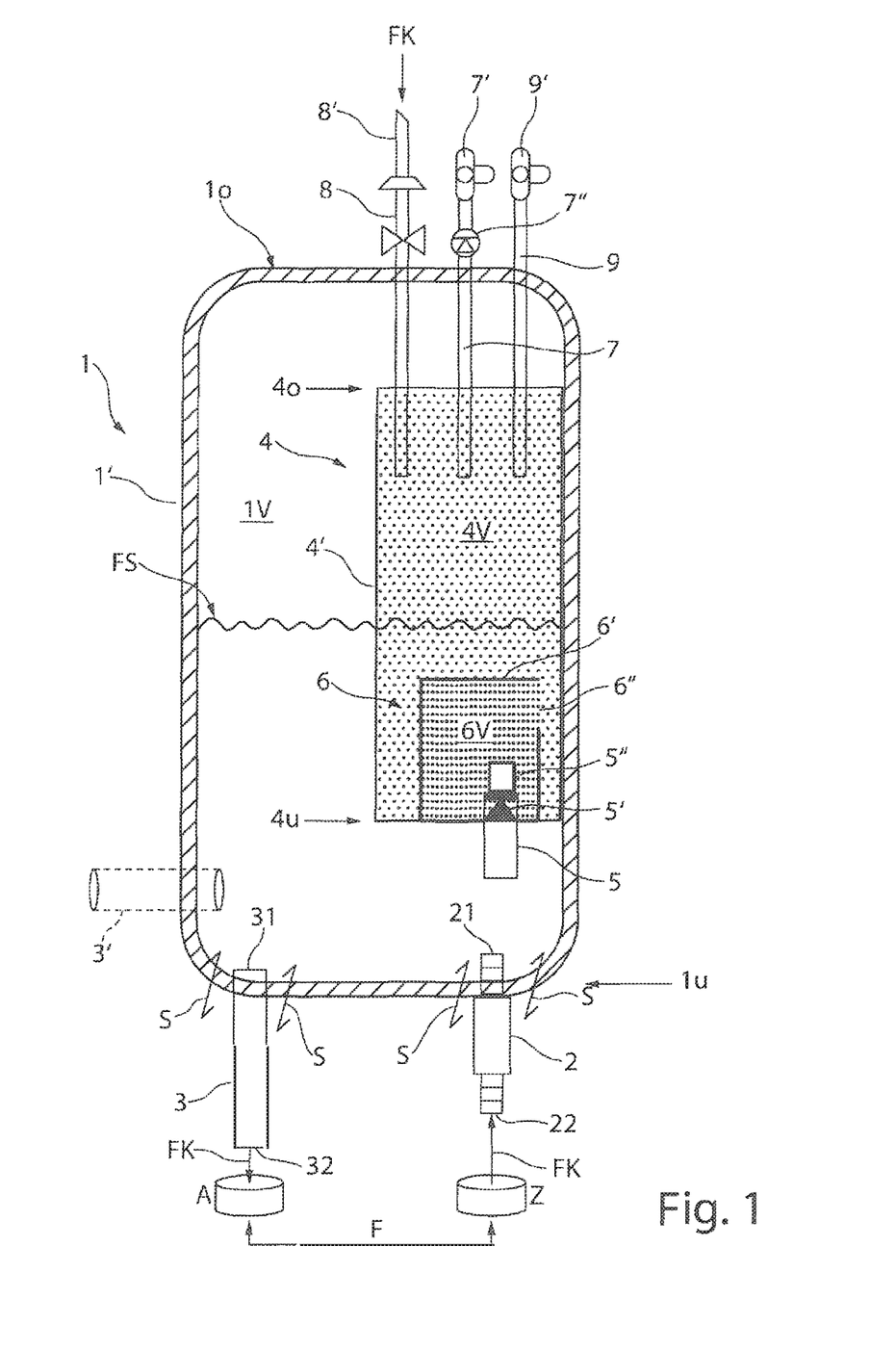
FIG. 1 shows a schematic illustration of the inventive device with a bag for filling a pump-operated, hollow line-supported liquid circuit.

FIG. 1 shows a highly schematic illustration of a bag 1, which a pump-operated, hollow line-supported liquid circuit F can be filled with a liquid FK without forming gas bubbles. For this purpose, the bag 1 has a light-transparent, elastic bag wall 1' that has a biocompatible and elastically deformable plastic material. The bag wall 1' at least partially encloses a bag volume 1V. The bag 1 is optionally designed in the form of a sack or conical bag that open on its upper side 1o. It is likewise possible to form the bag 1 with a completely closed bag wall 1' such that the inner bag volume 1V is also sealed in a fluid-tight manner on the upper bag edge 1o as illustrated in FIG. 1.

Two hollow channel sections 2 and 3 are arranged on the lower bag edge 1u, which lies diametrically opposite of the upper bag edge 1o, and locally passes through the bag wall 1' in a fluid-tight manner, wherein both hollow channel sections 2 and 3 respectively have an open channel end 21 and 31 located within the bag 1, as well as an open channel end 22 and 32 located outside the bag 1. Both hollow channel sections 2 and 3 respectively provide open access to the inner bag volume 1V.

A first filter insert 4 is additionally provided within the bag 1, wherein the filter wall 4' of this first filter insert has the form of a screening filter that preferably has a filter pore size between 20 and 200 µm, and particularly 40, 80 or 120 µm. In a first variation, the first filter insert is like the bag 1 itself designed in a bag-like or sack-like manner, that is the upper side 4o of the first filter insert 4 is open whereas the filter wall 4' otherwise encloses the first inner filter volume 4V on all sides. In a second variation, it is also possible to design the first filter insert 4 with a first filter wall 4' that completely encloses the first filter volume 4V as illustrated in FIG. 1.

On its lower end 4u, the first filter insert 4 features a fluid line section 5 that openly passes through the filter wall 4', wherein the outer wall of the fluid line section locally borders on the first filter wall 4' in a fluid-tight manner. The fluid line section 5 is preferably designed in the form of a short tube section having an elastic material such as PVC. A check valve 5' is preferably arranged along the fluid line section 5 in order to prevent liquid in the first filter volume 4V or a second filter volume 6V, which is described in greater detail below, from reaching the bag volume 1V. In addition, a flow restricting element 5" may be arranged on the open end of the fluid line section 5 leading into the filter volume 4V in order to reduce the flow cross section on the end of the fluid line section 5 and to thereby generate a local pressure increase along the fluid line section 5, which has a positive effect on the gas separation process.

In order to produce a separable fluid-tight connection between the fluid line section 5 and the channel end 21 of the hollow channel section 2, which is located within the bag and made of a harder material than the fluid line section, preferably of polycarbonate, the diameter ratios of the fluid line section 5 and of the hollow channel section 2 are adapted to one another in such a way that the flexible fluid line section 5 can be pushed over the channel end 21 of the first hollow channel section 2 in a fluid-tight manner. The required manipulations are carried out from the outside through the light-transparent and flexible bag wall 1'. The connection produced in the above-described manner can likewise be separated again with suitable manipulations carried out from the outside through the bag wall 1'.

The second hollow channel section 3 passing through the bag wall 1' is like the fluid line section 5 made of an elastic material, preferably of PVC, in order to produce a fluid-tight connection between this second hollow channel section and the channel end 21 of the first hollow channel section 2 located within the bag 1 by pushing the open channel end 31 of the second hollow channel section 3, which is located within the bag 1, over the open channel end 21 of the first hollow channel section 2 in a fluid-tight manner.

Alternative fluid-tight flange connecting mechanisms, which have a suitable design and are known in the art such as Luer-Lock connections, may naturally also be used for producing a separable fluid-tight connection between the fluid line section 5 and the first hollow channel section 2, as well as between both hollow channel sections 2 and 3.

In the exemplary embodiment illustrated in FIG. 1, the first and the second hollow channel section 2 and 3 are oriented parallel to one another and pass through the filter wall 1' at a distance from one another on the lower side 1u of the bag 1. It is preferred to arrange the second hollow channel section 3 such that it is inclined toward the first hollow channel section 2 in order to thereby simplify the connection between both hollow channel sections. As an alternative to the illustrated example, it would in this context also be conceivable to arrange the second hollow channel section 3 such that its longitudinal channel axis is in the region of the lateral filter wall 1' oriented orthogonal to the longitudinal channel axis of the second hollow channel section 2. In FIG. 1, this alternative arrangement is illustrated in the form of the second hollow channel section 3' drawn with broken lines.

According to a preferred embodiment, a second filter insert 6 is furthermore provided within the first filter insert 4, wherein the second filter wall 6' of this second filter insert completely or partially encloses a second filter volume 6V, into which the fluid line section 5 leads, together with the lower side 4u of the first filter wall 4'. The second filter insert 6 is like the first filter insert 4 is a screening filter and preferably has the same pore size as the first filter insert. The second filter insert 6 serves for reliably degassing fluid flows that contain gas and flow through the bag arrangement with high flow speeds amounting to five liters per minute and more, for example seven liters per minute.

The second filter insert 6 preferably has an opening 6" that faces away from the filter wall 4', wherein the liquid flow can reach the first filter volume 4V through the opening after a corresponding flow deviation. In this case, the second filter insert 6 not only serves for providing a first degassing stage, but also the flow deviation such that the liquid flow does not act upon the first filter wall 4' with a high flow speed.

A filling line 8 is provided for filling the bag 1 with liquid and passes through the open or closed upper bag edge 1o, as well as the upper side of the first filter insert 4o, such that the liquid supplied through the filling line 8 is initially introduced into the first filter volume 4V. The filling line 8 preferably features a piercer 8'. Furthermore, a degassing line 7 leads into the first filter volume 4V through the upper bag edge 1o and the upper side 4o of the first filter insert 4, wherein the separated gas fractions can respectively escape or be removed by suction through the degassing line. In an alternative embodiment, the degassing line 7 leads into the upper region of the bag volume 1V. The degassing line 7 preferably features a three-way valve 7' and a check valve 7". Depending on the intended use, additional fluid lines 9 with a three-way valve may lead into the first filter volume 4V or the bag volume 1V in accordance with the respective pump-operated, hollow line-supported liquid circuit F to be filled with a liquid. The filling line 8 and the degassing line 7 are advantageously arranged on the bag 1 in such a way that they respectively protrude into the bag volume 1V and into the filter volume 4V over the upper bag edge 1o. The additional fluid line 9, in contrast, may be arbitrarily arranged on the bag 1 depending on its technical purpose, wherein this additional fluid line may extend, for example parallel to the first hollow channel section 2 and openly leading into the bag volume 1V or into the filter volume 4V. It is also conceivable to provide a check valve along the additional fluid line 9 in order to prevent backflow.

The above-described bag-shaped device primarily serves for filling a hollow line-supported liquid circuit F, of which only a discharge line A and a supply line Z are representatively illustrated in FIG. 1, wherein the discharge and supply lines can be respectively connected to the open ends 22 and 32 of the first and second hollow channel sections 2 and 3 in a fluid-tight manner.

The filling process of the pump-operated, hollow line-supported liquid circuit F is carried out by initially producing a fluid-tight connection between the fluid line section 5 and the end 21 of the first hollow channel section 2. The bag 1 is then filled with a liquid FK through the filling line 8. During this process, the liquid FK flows through the first filter wall 4' and reaches the pump-operated, hollow line-supported liquid circuit F through the second hollow channel section 3, which is connected to the discharge line A in a fluid-tight manner.

The bag 1 is filled with liquid FK in such a way that a liquid level FS, which lies at least above the fluid line section 5, but preferably comprises the entire second filter volume 6V, appears within the bag 1. A preferred liquid level FS is indicated in FIG. 1, that is normal atmospheric ambient conditions exist above the liquid level FS. The filling process is completed as soon as the entire liquid circuit F is filled with liquid and the liquid level FS indicated in FIG. 1 approximately appears within the bag 1. Due to the at least one (not-shown) circulation pump integrated along the liquid circuit F, the liquid flows from the bag 1 into the first filter volume 4V, as well as into the second filter volume 6V if a second filter insert 6 is provided, through the discharge line A and the supply line Z. A gas separation respectively takes place as the liquid flows through the filter walls 6' and 4'. As a result, the liquid FK is completely degassed, that is free of gas bubbles, after it ultimately flows into the adjacent bag volume 1V through the first filter wall 4'.

The process of degassing the liquid circulating through the bag arrangement and the pump-operated, hollow line-supported liquid circuit connected thereto in a fluid-tight manner is completed after no further gas separation occurs within the first and second filter insert 4, 4. In the simplest case, this can be assessed by a mere visual inspection.

Furthermore, the fluid line section 5 is respectively disconnected or separated from the first hollow channel section 2 and a fluid-tight connection between the first and the second hollow channel section 3 is subsequently produced. The separating and connecting processes are carried out within the bag volume 1V filled with liquid FK such that any inclusion of gas bubbles whatsoever can be precluded during the connecting process.

After the fluid-tight connection between the first and second hollow channel sections 2 and 3 has been produced, the bag 1 is emptied and removed from the first and second hollow channel sections 2 and 3. For this purpose, predetermined breaking points S are provided within the bag wall 1'.

Figure 2:
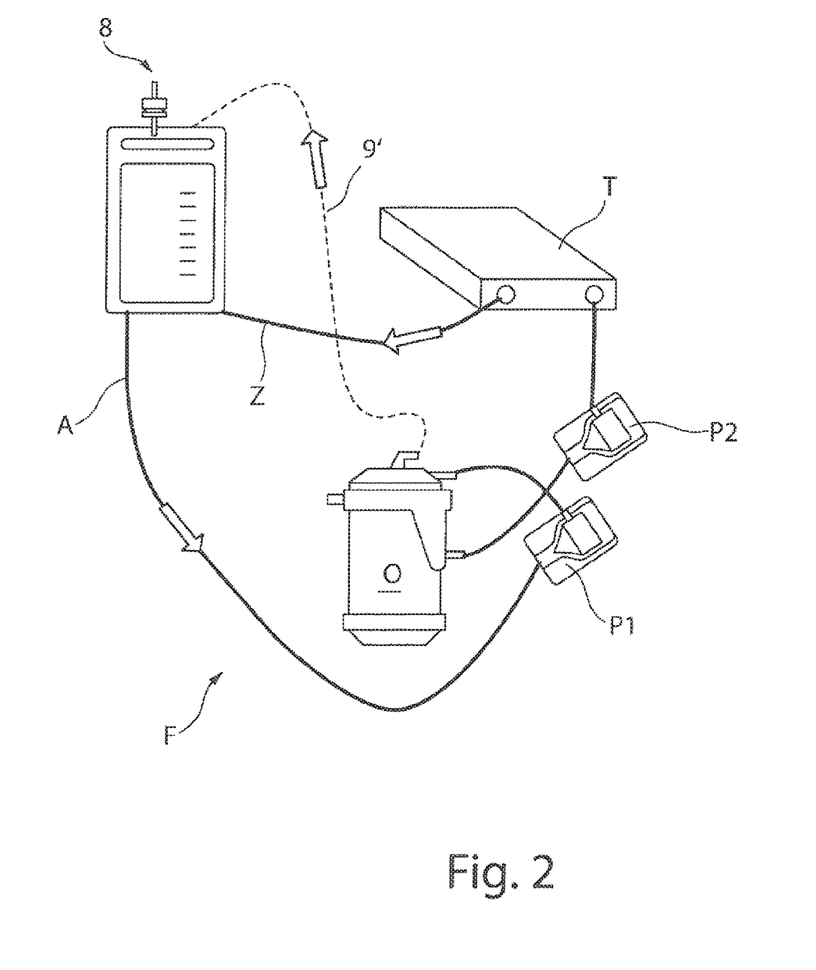
FIG. 2 shows an illustration of a filling process of an extracorporeal circulatory system with an oxygenator.

A preferred exemplary application of the inventive bag-shaped device is illustrated in FIG. 2. In this case, the bag-shaped device 1 serves for filling a pump-operated, hollow line-supported liquid circuit F that contains an oxygenator O, as well as a fluid line section referred to as table line T.

In a first step, the bag 1 is filled with a liquid through the filling line 8. During this process, the supply line Z of the pump-operated, hollow line-supported liquid circuit F is clamped off in order to prevent liquid from reaching the hollow line-supported liquid circuit F opposite to the transport direction defined by the pumps P1/P2. Due to the operation of the pump P1, the liquid flows from the bag 1 into the oxygenator O through the discharge line A, wherein the oxygenator features a shunt line 9' that serves for ventilating the oxygenator O and leads into the bag in the with a fluid line 9 as described above. After the oxygenator O has been filled accordingly, the second pump P2 is activated and the clamp along the supply line Z is released. Consequently, the liquid flowing out of the oxygenator O reaches the bag 1 through the fluid line section, which is combined into the table line T, and the supply line Z. The above-described degassing of the liquid flow with the help of the at least one filter insert, preferably two separate filter inserts, then takes place within the bag. After the degassing process has been successfully completed, the supply and discharge lines A, Z are connected in a fluid-tight manner and without forming gas bubbles by connecting the first and second hollow channel sections within the bag 1.

Due to the operation of the pumps P1/P2, the filling process can be completed within a very short time and it can also be ensured that the filling process takes place without forming gas bubbles.

REFERENCE LIST

1 Bag-shaped container, bag
1V Bag volume
1' Bag wall
1o Upper bag edge
1u Lower bag edge
2 First hollow channel section
3 Second hollow channel section
4 First filter insert
4V First filter volume
4' First filter wall
4o Upper filter edge
4u Lower filter edge
5 Fluid line section 5' Check valve
5" Flow restricting element
6 Second filter insert
6' Second filter volume
6V Second filter wall
6" Opening
7 Degassing line
7' Three-way valve
7" Check valve
8 Filling line
9 Fluid line
21 Open end of first hollow channel section within bag
22 Open end of first hollow channel section outside bag
31 Open end of second hollow channel section within bag
32 Open end of second hollow channel section outside bag
F Liquid circuit
FK Liquid
FS Liquid level
A Discharge line
S Predetermined breaking point
Z Supply line
P1/P2 Pump
O Oxygenator
T Tubing

The invention claimed is:

1. A container comprising a bag including a closed wall defining a sealed volume with the sealed volume receiving fluids under pressure, the bag including a wall containing a flexible region through which pass first and second hollow channels which are sealed to the wall, each channel including ends with each end opening into an interior of the volume, the ends being connectible together in a separable and fluid tight connection, a first filter within the sealed volume defining a first filter volume and including a first filter wall through which passes a tubular fluid line having fluid line openings, the fluid tubular line being connected to the first filter wall, one of the fluid line openings being connected to the sealed volume and another of the sealed filter openings being connected to the first filter volume; and
  an end of the first hollow channel located within the first volume is connected to be fluid tight to an end of the tubular fluid line and is separable from the end of the tubular fluid line.

2. The container according to claim 1 comprising:
  a second filter insert located within the first filter insert, at least partially encloses a second filter volume and includes a second filter wall into which the fluid tubular line is coupled to the first filter volume and the second filter wall is coupled with a fluid tight connection.

3. The container according to claim 2 wherein the second filter insert is fixed to at least one of the first filter insert and the fluid tubular line.

4. The container according to claim 1 comprising:
  the first and second hollow channels have ends disposed outside the sealed volume and which are respectively connected to a supply line and a discharge line of a liquid supply circuit including a fluid tight connection.

5. A method of use of a container according to claim 4 for filling the liquid supply circuit with a liquid with a pump without gas bubbles within the liquid in the first filter insert comprising:
  interrupting the pumping of liquid into the first filter insert so that the fluid connection is opened to provide two open ends.

6. The method in accordance with claim 5 comprising:
  connecting an oxygenator to the open ends and starting pumping of blood of a patient through the oxygenator to pump oxygenated blood into the volume of the container.

7. The container according to claim 1 comprising at least one degassing line coupled to the first filter volume.

8. The container according to claim 1 comprising at least one filling line coupled to the first filter volume for filling the first filter volume with fluid.

9. The container according to claim 1 comprising at least one degassing line and at least one filling line located on a wall section opposite to a section of the wall of the bag through which the tubular line section passes.

10. The container according to claim 9 wherein the bag comprises an opening on the wall section on which the at least one degassing line and the filling line is located or the bag is closed on the wall section of the bag or the degassing line and the filling line pass through the wall section with a fluid tight connection to the wall section.

11. The container according to claim 1 wherein the first filter insert is fixed to the bag.

12. The container in accordance with claim 1 wherein the flexible region comprises transparent plastic.

13. A method for filling a pump-operated liquid circuit without the formation of gas bubbles in the liquid circuit in which the liquid circuit has been interrupted by disconnecting the liquid circuit into two parts with one of the parts being a supply line and another of the parts being a discharge line, each line having an end opening into the liquid circuit with the liquid circuit during operation of the pump pumping liquid, the liquid circuit comprising a container including a bag having a wall defining a sealed bag volume with the sealed volume receiving pumped fluids under pressure, the bag including a wall containing a flexible region through which pass first and second hollow channels which are sealed to the wall, each channel including ends with each end opening into an interior of the volume, the ends being connectible together in a separable fluid connection, a first filter within the sealed volume defining a first filter volume and including a first filter wall through which passes a tubular fluid line having fluid line openings, the fluid tubular line being connected to the first filter wall, one of the tubular fluid line openings being connected to the sealed volume and another of the fluid line openings being connected to the first filter volume and an end of the first hollow channel located within the first volume being separable and connectable to an end of the tubular fluid line and when connected to the end of the tubular fluid line is fluid tight, the method comprising:
  connecting the supply line to the first hollow channel and connecting the discharge line to the second hollow channel with the connecting being fluid tight;
  filling the liquid circuit with liquid introduced into the first filter volume with liquid flowing from the first filter volume into the sealed volume with the liquid flowing from the discharge line into the supply line and then liquid flows into the first filter volume and then into the filter volume;
  continuing filing of the filter volumes until are partially filled;
  continuing pumping flow in liquid supply circuit and through the bag until the fluid has passed at least once through the first filter wall; and
  separating a connection between the first hollow channel and the tubular fluid line and making a fluid-tight connection between the first and second hollow channels within the bag during fluid flow through the liquid circuit or after a standstill of liquid flow in the fluid flow circuit with the separation and connection of the connection take place with the sealed bag volume filled with the liquid.

14. The method according to claim 13 comprising pumping the liquid through the fluid circuit to flow through a second filter wall of a second filter located within first filter volume and then through the first filter wall.

15. The method according to claim 13 comprising connecting and oxygenator into the fluid circuit and filling the oxygenator with the fluid in the fluid line.

16. The method according to claim 13 comprising connecting the hollow channels within the bag and then either emptying the bag or at least partially disconnecting the bag from the hollow channels.

17. The method according to claim 13 comprising completely surrounding at least the tubular fluid line with the pumped fluid and then completing filling the fluid circuit.

18. The method according to claim 13 comprising pumping all of the liquid contained in the fluid line and the bag is pumped through the first filter wall until a reduced amount of gas bubbles in the pumped liquid is reached as a consequence of filtering of the gas bubbles by the first filter wall.

* * * * *